United States Patent

Reierson

[11] Patent Number: 5,846,923
[45] Date of Patent: Dec. 8, 1998

[54] POLYAMPHOTERIC PHOSPHATE ESTER SURFACTANTS

[75] Inventor: Robert Lee Reierson, Cranbury, N.J.

[73] Assignee: Rhodia Inc., Cranbury, N.J.

[21] Appl. No.: 889,265

[22] Filed: Jul. 8, 1997

[51] Int. Cl.⁶ ........................................................ C11D 1/34
[52] U.S. Cl. ............................................ 510/467; 558/158
[58] Field of Search ............................. 510/467; 558/158

[56] References Cited

U.S. PATENT DOCUMENTS

| | | | |
|---|---|---|---|
| 2,773,068 | 12/1956 | Mannheimer | 260/309.6 |
| 2,781,354 | 2/1957 | Mannheimer | 260/309.6 |
| 3,941,817 | 3/1976 | Chakrabarti | 260/404.5 |
| 4,705,843 | 11/1987 | Stammann et al. | 528/212 |
| 5,332,528 | 7/1994 | Pan et al. | 252/548 |
| 5,523,024 | 6/1996 | Garabedian, Jr. et al. | 252/547 |
| 5,550,274 | 8/1996 | Reierson | 558/110 |
| 5,554,781 | 9/1996 | Reierson | 558/110 |

FOREIGN PATENT DOCUMENTS

| | | |
|---|---|---|
| 277269 B6 | 12/1992 | Czechoslovakia . |
| 14689 A1 | 8/1980 | European Pat. Off. . |
| 33715 A1 | 8/1981 | European Pat. Off. . |
| 43790 A1 | 1/1982 | European Pat. Off. . |
| 2154458 | 5/1972 | Germany . |
| 3330679 A1 | 3/1984 | Germany . |

OTHER PUBLICATIONS

Menger et al.; Gemini Surfactants: A New Class of Self--Assembling Molecules. J. Am. Chem. Soc., 115; No. 22 (1993) 10083–10090.

Zhu et al.; Preparation and Properties of Glycerol–Based Double or Triple–Chain Surfactants with Two Hydrophilic Ionic Groups. JAOCS, 69; No. 7 (Jul. 1992) 626–632.

Zhu et al.; Preparation and Properties of Double–or Triple–Chain Surfactants with Two Sulfonate Groups Derived from N–acyldiethanolamines. JAOCS, 68; No. 7 (Jul. 1991) 539–543.

Zhu et al.; Preparation and Surface–Active Properties of New Amphipathic Compounds with Two Phosphate Groups and Two Long–Chain Alkyl Groups. JAOCS 68; No. 4 (Apr. 1991) 268–271.

Zhu et al.; Preparation and Surface Active Properties of Amphipathic Compounds with Two Sulfate Groups and Two Lipophilic Alkyl Chains. JAOCS, 67; No. 7 (Jul. 1990) 459–463.

Aldrich Chemical Company Catalog, p. 946, 1994 No Month Available.

*Primary Examiner*—Paul Lieberman
*Assistant Examiner*—John R. Hardee
*Attorney, Agent, or Firm*—Craig M. Bell; John Daniel Wood

[57] ABSTRACT

A surfactant composition comprising the formula:

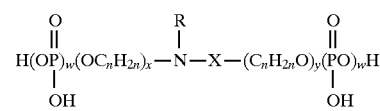

wherein X is:

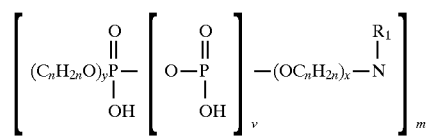

wherein R and $R_1$ independently represent the same or different $C_1$ to $C_{36}$ straight or branched chain alkyl, alkene, aryl, alkylaryl and arylalkyl, said R and $R_1$ optionally further characterized as containing ether, thioether, polyalkylene oxide, amine or quaternary ammonium, amide or ester groups; or are substituted thereby with the open valence filled by $R_3$ wherein $R_3$ is hydrogen or R, n is a whole number from 2 to about 4, m is 0 to 10, v is 0 or 1, w is 0, 1, or 2 and x and y are whole number integers of from 1–50.

More specifically, R and $R_1$ can individually represent:

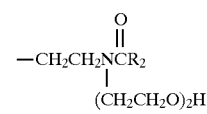

wherein $R_2$ independently is selected from the group defined by R and z is 0 or a whole integer.

17 Claims, No Drawings

POLYAMPHOTERIC PHOSPHATE ESTER SURFACTANTS

FIELD OF THE INVENTION

This invention relates to a novel group of amphoteric surfactants having at least two hydrophilic groups and at least two hydrophobic moieties per molecule useful as emulsifiers, detergents, dispersants, hydrotropes, wetting agents, gellants, corrosion inhibitors and solubilizing agents.

BACKGROUND OF THE INVENTION

Surfactants are well known materials which can be generally described as having a hydrophilic group and a hydrophobic moiety per molecule. A wide variety of these materials are known and are classified as anionic, cationic, nonionic and amphoteric. They are well known to be useful as emulsifiers, detergents, dispersants and solubilizing agents in the field of cosmetics, textile treatment, industrial and personal cleaning preparations, and the like.

In many surfactant containing compositions, such as personal cleaning preparations, mildness is a sought after characteristic. The amphoteric surfactants are particularly important in fulfilling that need. Amphoteric surfactants are compounds uniquely structured to function as cationic surfactants in acid pH environments and anionic surfactants at alkaline pH. At the isoelectric point, the amphoteric surfactants are charge balanced, internally neutralized zwitterions, a factor contributing to their mildness. These compounds are well known and some are disclosed in U.S. Pat. Nos. 3,941,817 to Chakrabarti; 4,705,843 to Stammann, et al; and 2,781,354 and 2,773,068 both to Mannheimer, which are illustrative. Amphoteric surfactants are also biodegradable and therefore are ecologically compatible.

Surfactants generally are compounds having one hydrophilic "head" group and one hydrophobic "tail" moiety. Recently, a group of compounds having two hydrophilic groups and two hydrophobic moieties have been introduced. These have become known as "gemini surfactants" in the literature [Chem Tech; 3, 30, (1993) and J. Am. Chem. Soc. 115, 10083 (1993)], and the references cited therein. Since their introduction, cationic and anionic "gemini surfactants" have been disclosed. Other surfactant compounds having two hydrophilic groups and two hydrophobic moieties have been disclosed but not specifically referred to as gemini surfactants.

Gemini surfactants contain two hydrophilic heads and two lipophilic chains linked by a relatively short bridge. Because gemini surfactants demonstrate very special physical properties such as unusually low critical micelle concentrations (cmc) and high $pC_{20}$ values in aqueous media, they have drawn significant attention. It has been reported that gemini surfactants have cmc values about two orders of magnitude lower than single chain analogues and are about 1000 times more efficient at reducing the surface tension as measured by the $pC_{20}$. Beside these outstanding physical properties, selected gemini surfactants can be very effective, are also biodegradable, and to a certain extent, available from renewable resources such as natural oils and sugars.

Sulfate, phosphate, and carboxylate surfactants are currently disclosed in the literature [JAOCS 67, 459 (1990); JAOCS 68, 268 (1991); JAOCS 68, 539 (1991); and JAOCS 69, 626 (1992)].

The phosphation of secondary aliphatic alcohols is difficult, especially with phosphoric anhydride, because dehydration to olefins occurs. The water thus produced results in higher residual levels of phosphoric acid and unphosphated material. The dehydration side reaction is reduced by substitution of an ether or alkylamine on the carbon adjacent (beta) to the hydroxyl carbon. The present invention is directed toward compounds which are characterized by primary hydroxyl groups or higher adducts based on the reaction of the alcohol or an alkylamine with an alkylene oxide.

Sulfation similarly can lead to dehydration by-products and carboxymethylation of secondary hydroxyl groups is also difficult, resulting in low yields of the desired compounds.

Due to the need for new, more effective and efficient surfactants, as well as the need for mild surfactants which are biologically compatible with ecologically sensitive environments, a new class of compounds has been developed which demonstrates improved surface-active properties that are further characterized as mild and environmentally benign.

Tsubone et al. [JAOCS 66, 829, (1989)] disclose a series of novel amphoteric surfactants comprised of the sodium salts of 2-(N-alkyl-N-methylamino)-ethane phosphates that were prepared through the reaction of alkylbromides with N-methylaminoethanol followed by the addition of phosphoric anhydride to the phosphate salt, followed by hydrolysis and neutralization with sodium hydroxide.

U. S. Pat. No. 4,824,603 to Möller et al. teaches and claims a novel class of phosphobetaine surfactants. These contain one quaternary ammonium group with from one to three phosphate ester groups in the surfactant molecule and are disclosed as being useful in body or hair shampoos. U. S. Pat. Nos. 5,554,781 and 5,550,274 to Reierson disclose the efficient preparation of a unique phosphation reagent which is utilized to prepare alkyl phosphate esters having a high monoalkyl content in combination with low dialkyl phosphate, phosphoric acid and residual alcohol content.

The characteristic advantages reported for the known gemini surfactants are their higher efficiency in forming micelles as indicated by the low critical micelle concentration and higher surfactant activity as measured by the low concentration required to reduce water surface tension by 20 dyne/cm ($C_{20}$; $pC_{20} = -\log C_{(\Delta\gamma=20)}$). The low concentration of surfactant molecules that are free outside the micellar structures ($\leq$cmc) suggests a lower irritancy potential and the higher surface activity indicates less surfactant is required to significantly reduce the surface tension as needed for a given application.

Problems exist however, in the preparation of the gemini surfactants known in the art. First of all, the synthesis routes are multi-step and frequently involve costly reagents, making the gemini surfactants often relatively uneconomical vis-a-vis conventional surfactants. Secondly, the water solubility and/or dispersability of these surfactants frequently is relatively low.

It is an object of the present invention to prepare a novel series of gemini and higher order oligomeric surfactant structures that provide superior surface activity, low cmc and $C_{20}$ values, are of low irritancy and toxicity, and are economically feasible to produce. More specifically, it is an object of the present invention to produce novel poly (alkylamine bis-ethoxylate phosphate) amphoteric surfactants in which the phosphate species serves both as the anionic hydrophilic group and the bridging group between the hydrocarbon chains.

SUMMARY OF THE INVENTION

A novel class of gemini and higher order oligomeric polyamphoteric surfactants are comprised of poly (alkylamine bis-ethoxylate phosphates) in which the phosphate species serves as both the anionic hydrophilic group and bridging group between the hydrocarbon chains. The novel surfactants are prepared by combining the coupling of the hydrophobic tails and the introduction of the anionic hydrophilic groups in one step on an amine bis-ethoxylate starting material to produce the polyamphoteric product. These surfactants are particularly useful as lubricants, gellants, and anti-scale additives in oil field drilling applications, as well as friction reducing or anti-wear lubricant additives, corrosion inhibitors, cleaning and emulsification agents and the like.

wherein $R_2$ independently is selected from the group defined by R and z is 0 or a whole integer.

The surfactants are prepared by phosphation with phosphoric anhydride or by following a reaction procedure similar to the phosphation sequence set forth in commonly owned U. S. Pat. Nos. 5,554,781 and 5,550,274 to Reierson which are hereby incorporated by reference. The alkyl amine bis-ethoxylate essentially is combined with phosphoric anhydride in an equimolar amine to phosphorus ratio (four moles amine per mole $P_4O_{10}$) to produce the components in the theoretical amounts shown.

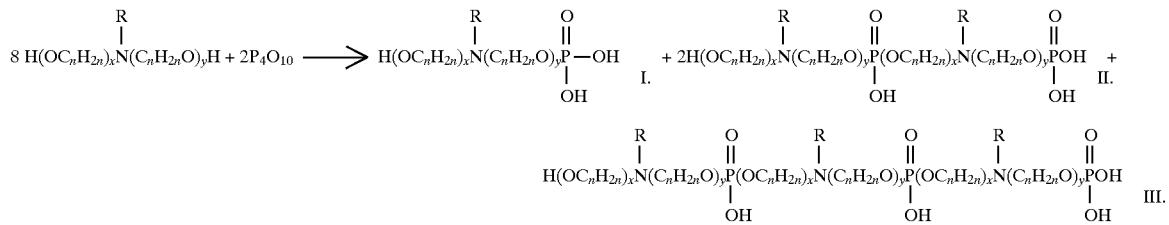

DETAILED DESCRIPTION OF THE INVENTION

The present invention concerns the preparation of novel poly(alkylamine bis-ethoxylate phosphate) amphoteric surfactants in which the phosphate species serves as both the anionic hydrophilic group and the bridge between the two hydrocarbon chains. Generally, the surfactant compositions of the present invention may be structurally represented by the formula:

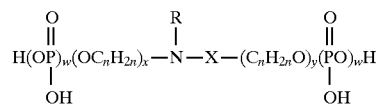

wherein X is:

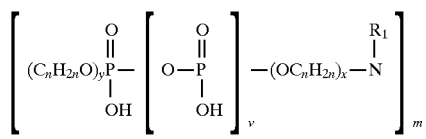

wherein R and $R_1$ independently represent the same or different $C_1$ to $C_{36}$ straight or branched chain alkyl, alkylene, aryl, alkylaryl and arylalkyl, said R and $R_1$ optionally further characterized as containing ether, thioether, polyalkylene oxide, amine or quaternary ammonium, amide or ester groups; or are substituted thereby with the open valence filled by $R_3$ wherein $R_3$ is hydrogen or R, n is a whole number from 2 to about 4, m is a number of from 1 to 10, v is 0 or 1; w is 0, 1, or 2 with the further stipulation that both w's cannot be 0 and x and y are whole number integers of from 1–50.

More specifically, R and $R_1$ can individually represent:

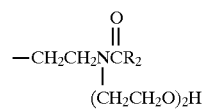

wherein R is independently selected from the group consisting of a saturated or unsaturated aliphatic $C_1$–$C_{36}$ straight or branched hydrocarbon chain, a phenyl, a substituted phenyl, a phenyl $C_1$–$C_6$ alkyl, and a substituted phenyl $C_1$–$C_6$ alkyl, wherein the phenyl substituent group(s) each have a total of 1 to 30 carbons and wherein each substitution may be a saturated or unsaturated straight or branched carbon chain, a phenyl, an alkyl phenyl, a phenyl alkyl or an alkyl phenyl alkyl group; wherein each carbon chain may contain heteroatomic functionality selected from the group consisting of:

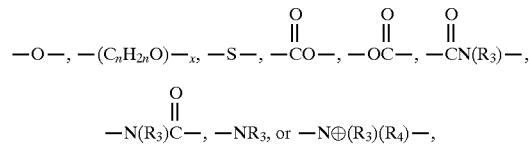

or may be substituted thereby with the open valence filled by $R_3$;

wherein x and y are integers from 1 to 50, n is a number from 2 to 4 and may be the same or different for each alkylene oxide unit and $R_3$ and $R_4$ are independently hydrogen or R.

A mixture would be expected to be formed as is usual for phosphation reactions, but because of the tendency of each $P_4O_{10}$ molecule to react with six hydroxyl groups to produce two moles of monoalkyl phosphate and two moles of dialkyl phosphate, on average, half of the phosphates become the dialkyl bridging groups and the other half become monoalkyl terminal groups, under anhydrous conditions. Within the range of degrees of ethoxylation in which x and y are positive integers which may be (but usually are not) equal, two single hydroxyethyl groups (x,y=1) would give a more hindered dialkyl phosphate, so the longer ethoxylate chains (x,y>1) would be more likely to be coupled by the dialkyl phosphate group. The fatty amine ethoxylation process is designed to favor production of bis-ethoxylates with minimization of the secondary amine monoethoxylate by-products. These amine ethoxylates then, are preferred over products contaminated by secondary fatty amines which have only a single ethoxylate chain, although minor amounts of the secondary amines can be tolerated as terminal groups.

As is evident from the equation, this mixture is not strictly a "gemini surfactant" composition as is known in the art, although one of the components, the dimer II, would be such a structure. The composition is much more complex and the dimer separation and complete characterization of the dimer or other individual components is difficult and unnecessary because the product component structures and composition would be optimized for each specific application and would be commercialized as the mixture based on its performance.

The mixture's phosphate composition can be varied in two ways. First, by increasing the ratio of phosphoric anhydride to amine, the average chain length is increased toward the "trimer", as depicted in structure III, supra, toward the tetramer, or even higher poly(amphoteric) oligomers. Each protonated amine has a corresponding alkyl phosphate anion. If water were present, the average chain length would be less, and more monomer, as depicted in structure I, would be produced. Secondly, the phosphation reagent might be changed progressively through the compositions as described in U. S. Pat. No. 5,554,781 to Reierson down to a point approaching the commercial 115% polyphosphoric acid level. Along with this change and the resulting shift toward higher levels of monoalkyl phosphate, phosphoric acid, and unphosphated amine ethoxylate end groups as well as lower levels of dialkyl phosphate content, the ratio of phosphation reagent to amine could be increased to produce a composition in which the alkyl phosphate groups are in molar excess over the amine groups. That is, the free hydroxyl groups in I, II and III are converted to phosphate groups which would then be neutralized by added base. The higher anionic phosphate ester content would increase the water solubility of the components.

Alternate ways to change the water solubility and modify other properties of these surfactants would be to alter the structure of the amine ethoxylate by increasing the degree of ethoxylation or substitute in part or whole a higher oxide (e.g. propylene oxide, for the ethylene oxide), incorporate a hydrophilic group such as an amide or polyether chain into the R group, change the chain length or chain branching, etc. Increasing hydrocarbon content by use of longer chain groups or substitution of higher alkylene oxides would contribute to lower water but higher oil solubility.

Examples have been prepared based on cocoamine and tallowamine bis-ethoxylates which have the desirable properties characteristic of gemini surfactants. Both products of these examples had very low critical micelle concentrations and high surface tension reduction efficiencies as measured by the $pC_{20}$ values, which are characteristic of gemini surfactants. The low foaming is characteristic of dialkyl phosphates. This surface tension reduction efficiency and low foam potential is very desirable for oil field drilling lubricant applications. Other potential applications of the poly(alkylamine bis-ethoxylate phosphates) might be as gellants, anti-scaling agents, lubricating oil additives for reduction of friction or wear, corrosion inhibitors, viscosity control (shear sensitive thickeners), cleaning agents, emulsification agents in emulsion polymerization, metal cleaning, cutting or grinding aids and so forth.

In the past, gemini surfactants have usually been prepared by coupling the hydrophobic tails in one step, then converting available reactive sites, usually hydroxyl groups, to anionic hydrophilic groups, commonly sulfate, sulfonate or carboxylate. In the present invention, the coupling reaction and the introduction of the anionic hydrophile are both accomplished in a single step with readily available amine ethoxylate starting materials to produce a polyamphoteric product.

The essential components in the polyamphoteric product are the basic and acidic groups, the amine and phosphate, respectively. Ethoxylation of primary amines to give two ethoxylate chains is a convenient, cost-effective process to provide the bis(hydroxyl) moiety necessary to form the poly(amphoteric) structure. Other ways to accomplish this would be to prepare bis(hydroxyethyl) intermediates containing amide groups from fatty esters (or acids) and alkanol diamines as follows:

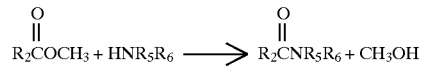

wherein $R_2$ independently is selected from the group defined by R, and $HNR_5R_6$ represents
a) $H_2NCH_2CH_2NHCH_2CH_2OH$;
b) $H_2NCH_2CH_2N(CH_2CH_2OH)_2$;
c) $HOCH_2CH_2NHCH_2CH_2NHCH_2CH_2OH$ (the monoamide can be prepared selectively),
d) $HOCH_2CH_2NHCH_2CH_2N(CH_2CH_2OH)_2$, or
e) $H_2NCH_2CH_2CH_2N(CH_2CH_2OH)_2$ The remaining active hydrogens of the aminoalkylamide are then reacted with ethylene oxide. Since the hydroxyethylation rate of the secondary amide is slower than for the amine, the products of amines a) and b) are similar (IV, z=0) as would be the products of c) and d) (IV, z=1). The cleanest product would be derived from a) aminoethylethanolamine since it is commercially available as a $99^+\%$ pure material. The next three are products derived as a mixture from production of a). The symmetrical product, c) can be obtained from the mixture by recrystallization, leaving b) as the principal remaining component, if desirable or necessary. The product structures would be:

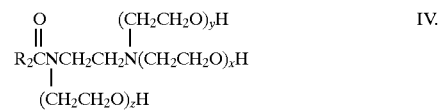

wherein x, y are positive integers and z=0 or a whole number.

The simplest phosphate-linked polyamphoterics derived from aminoethylethanolamine (a) would be similar to dimer structure II in which the amine alkyl group R would contain an amide, as depicted in structure V.

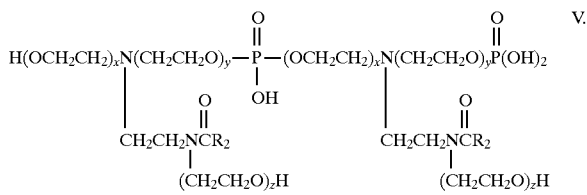

wherein $R_2$ has been hereinbefore defined.

Considering the difficulty frequently encountered in phosphation of the simple hydroxyethylamides in which the carbon beta to the hydroxyl is amide substituted, it is less likely that the amide hydroxyethyl group (z=1) in this more complicated structure would be phosphated, but it should still contribute to water compatibility and mildness.

Ester groups could be incorporated through the esterification of amine or diamine polyols provided that at least two hydroxy-functional chains remain for formation of the polyamphoteric structure. Related structures in which the amide group would be replaced by an ether or polyether group would be based, for instance, on (3-aminopropyl)alkyl ether and ether diamine ethoxylates. Substitution of mercaptans for the initial alcohol in this series would similarly provide a sulfide group.

Additional phosphate-linked species would be the intermediate pyrophosphates or polyphosphates which would persist from the use of an excess of the phosphation reagent under conditions which did not drive the reaction to completion, as set forth in structure VI.

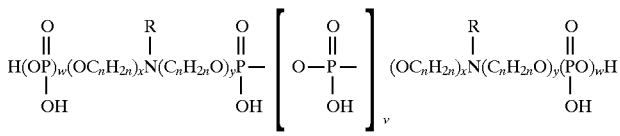

VI.

Since these pyrophosphate linkages (v=1) are reasonably stable to hydrolysis if the pH is neutral, they also are effective in forming phosphate-linked gemini surfactants and would be more hydrophilic than the simple dialkyl phosphate bridge (v=0). The pyrophosphate group may also be an end group (w=2) in place of the simple orthophosphate (w=1), where it similarly would contribute a more easily hydrated, higher ionic charge density "head" group at neutral pH.

The surfactants of the present invention offer wide structure-performance versatility including superior surface activity, and hence they can be used alone as the essential surfactant component.

It has also been unexpectedly found that blends of the compounds of the invention as defined hereinbefore can be made with certain conventional well known anionic, nonionic, cationic and amphoteric surfactants that provide synergistic results that can be demonstrated in relation to critical micelle concentration and surface tension reducing ability, fluid thickening or foam stabilization.

Examples of the nonionic surfactants useful as blends herein include fatty acid glycerine esters, polyglycerine fatty acid esters, higher alcohol ethylene oxide adducts, single long chain polyoxyethylene alkyl ethers, polyoxyethylene alkyl aryl ethers, polyoxyethylene lanolin alcohol, polyoxyethylene fatty acid esters, polyoxyethylene glycerine fatty acid esters, polyoxyethylene propylene glycol fatty acid esters, polyoxyethylene sorbitol fatty acid esters, polyoxyethylene castor oil or hardened castor oil derivatives, polyoxyethylene lanolin derivatives, polyoxyethylene fatty acid amides, polyoxyethylene alkyl amines, alkylpyrrolidones, glucamides, alkylpolyglucosides, mono- and dialkanol amides, polyoxyethylene alcohol mono- or diamides and alkylamine oxides.

Examples of the anionic surfactants useful as blends herein include fatty acid soaps, ether carboxylic acids and salts thereof, alkyl or aryl sulfonate salts, α-olefin sulfonate salts, sulfonate salts of higher fatty acid esters, higher alcohol sulfate ester salts, fatty alcohol ether sulfate salts, higher alcohol phosphate ester salts, fatty alcohol ether phosphate ester salts, sulfosuccinate esters, fatty acid isethionates or taurates, condensates of higher fatty acids and amino acids, and collagen hydrolysate derivatives.

Examples of the cationic surfactants useful herein include alkyltrimethylammonium salts, dialkyldimethylammonium salts, alkyldimethylbenzylammonium salts, alkylimidazolinium salts, alkylpyridinium salts, alkylisoquinolinium salts, benzethonium chloride, and acylamino acid type cationic surfactants. Examples of the amphoteric surfactants used herein include the amino acids, betaines, sultaines, phosphobetaines, imidazoline-type amphoteric surfactants, soybean phospholipids, and yolk lecithins.

In addition to the foregoing surfactants, any of the commonly used auxiliary additives may be added to the surfactants of the invention or blends thereof with other surfactants as disclosed herein. Such auxiliary additives may be suitably chosen for a desired composition and generally include inorganic salts such as Glauber salt and common salt, builders, humectants, solubilizing agents, UV absorbers, softeners, chelating agents, and viscosity modifiers.

The polyamphoteric surfactants of the present invention exhibit greater surface tension reduction, lower toxicity, and excellent compatibility with other anionic, cationic and nonionic surfactants, and being extremely mild and non-irritating to both eyes and skin as well, are adaptable for use in products ranging from cosmetics to industrial applications and are usable wherever amphoteric surfactants have found use. The structural diversity allows adaptation to many applications.

These products are useful in non-irritating shampoos or cleansing agents, including baby shampoos, hair and body shampoos, bubble baths, bar soaps, bath gels, hair conditioning gels, lotions, liquid detergents, hand wash dish detergents, skin creams and lotions, make-up removal creams and lotions, and other washing and cosmetic products that contact the skin as well as bleach activators, bleach stabilizers and the like.

In addition, the compounds and compositions of the invention can be used in connection with hard surface cleaners, high electrolyte cleaners, emulsion polymerization, liquid and bar soap, laundry and automatic dishwasher, bottle washing and carpet shampoo detergents, water-based lubricants, metal cleaning, oil well drilling lubricants and the like.

The following examples are provided to specifically teach and define how to synthesize representative compounds of the polyamphoteric surfactants of the present invention. They are for illustrative purposes only and it is understood that there are many variables that can be altered or changed in the process parameters and starting materials that will result in compositions not contemplated therein. It is to be understood that to the extent any such changes do not materially alter the structure and/or function of the final product, they are considered as following within the spirit and scope of the invention as recited by the claims that follow.

EXAMPLE 1

Preparation of Cocoamine Polyoxyethylene (POE) Bis-ethoxylate Phosphate by Phosphoric Anhydride ($P_4O_{10}$)

An oven dried apparatus consisting of a 2L, 4-necked, round bottomed flask, a paddle stirrer, thermocouple, pressure equalizing screw-feed powder addition funnel and a Claisen adapter containing an argon gas inlet fed through a 12" stainless steel needle inserted into a stopper and outlet through a silicone oil filled bubbler tube was assembled while warm and flushed with argon for an hour period with heating to provide a system free of moisture. The flask was quickly charged with 903.44 g of Rhodameen C-5 ethoxylated fatty cocoamine (2.23 mole) and the funnel charged with 163.62 g phosphoric anhydride. Of this charge, 159.19 g (0.56 mole) was added to the stirred liquor over a 25 minute period. The slurry was warmed in an oil bath to 110° C. within 90 minutes where it was maintained for 30 hours.

Analysis of the viscous liquor by $^{13}C$- and $^{31}P$-nuclear magnetic resonance (NMR) spectroscopy showed approximately one-fourth of the original hydroxy content remained, as expected, with the rest having been converted to phosphate. The normalized phosphate molar composition was 54.6% monoalkyl phosphate, 36.2% dialkyl phosphate, 7.4% symmetrical P,P'-dialkylpyrophosphate and only 1.7% phosphoric acid. The product composition, though a complex mixture, therefore consists of a slight molar excess of the monoalkyl phosphate end groups with a significant proportion of the phosphate groups as the dialkyl phosphate and symmetrical dialkyl pyrophosphate, serving to link the alkyl chains together. Notably, the free phosphoric acid content was very minimal.

EXAMPLE 2

Preparation of Tallowamine POE Bis-ethoxylate Phosphate $P_4O_{10}$

Following the same procedure set forth in Example 1, 11.79 g (0.042 mole) phosphoric anhydride and 99.18 g Rhodameen T-7 ethoxylated fatty tallowamine (0.169 mole) were combined in a 250 ml, 4-necked, round-bottomed flask under a dry, argon atmosphere and the slurry was warmed to 80° C. where it was maintained for 16 hours. Analysis of the viscous liquid by $^{31}P$-NMR spectroscopy showed it to contain only 17.6 mole % orthophosphate, 39.4% pyro- and polyphosphate chain end groups and 39.2% internal polyphosphate phosphorus groups. The reaction was then continued at 110° C. for 21 hours.

Overlapping signals in the $^{13}C$-NMR spectrum precluded definitive analysis but the $^3P$-NMR spectrum clearly showed the product mixture to be essentially free of residual phosphoric acid and approximately half of the phosphate groups served to couple the chains through dialkyl ortho-phosphate and P-P'-dialkyl pyrophosphate links.

EXAMPLE 3

Preparation of CocoaminePolyethylene Oxide Bis-ethoxylate Phosphate by a Mixed Phosphation Reagent To prepare a more water soluble product, the ethoxylated fatty acid tallowamine of Example 2 was phosphated by a mixed reagent consisting of approximately equal moles of amine and phosphorus as a combination of 105% polyphosphoric acid and phosphoric anhydride.

In the manner as described in Example 1, a 500 ml, 4-neck round-bottomed flask was charged with 244.17 g Rhodameen C-5 ethoxylated fatty acid tallowamine (0.603 mole, hydroxyl no. 277.3) and 56.03 g Super Phos® 105 (105% polyphosphoric acid, 0.600 equivalent phosphorus) was added drop-wise to the stirred liquor under argon atmosphere over a two hour period. The mixture was warmed to 50° C. to maintain stirring, then heated to 60°–65° C. for two hours to produce a uniform solution. The liquor was cooled back to 50° C. and 44.24 g phosphoric anhydride (0.156 mole; 0.623 equivalent phosphorus) was added over a three and one-half hour period during which the temperature rose to 58° C. External heat was then applied to gradually raise the liquor temperature to 90° C. where it was held for 90 minutes, then raised to 100° C. and 110° C. over successive two hour periods, where it was maintained for 16 and one-half hours.

Analysis of the product mixture by $^{13}C$-NMR spectroscopy showed that about 75% conversion of the 1.206 moles of alcohol had been achieved. About 80% of the hydroxyls on the polyethoxylate chains and 60% of the monoethoxylate hydroxyl groups had reacted, showing the slight preference for the former. The $^{31}P$-NMR spectrum results also indicated that about 75% of the alcohol groups had been converted with the molar ratio between ortho- and pyro-phosphates being 88:12 and the normalized molar equivalent distribution being 0.226 phosphoric acid, 0.020 pyrophosphoric acid, 0.565 monoalkyl phosphate, 0.061 monoalkyl pyrophosphate and the bridging groups being 0.090 dialkyl phosphate and 0.038 dialkylpyrophosphate. This is extreme because the gemini surfactants linked by the dialkyl orthophosphate and the P,P'-dialkyl pyrophosphate are relatively minor components, about 13 mole percent in total. The water solubility, however, was enhanced 7-fold compared to the product of Example 1.

EXAMPLE 4

Evaluation of the Poly(Alkylamine Bis-ethoxylate Phosphate)Mixtures

The properties of the aminoalkyl phosphate polyampho-teric mixtures prepared in Examples 1 and 2 were determined. Comparison of the properties to those of known gemini surfactants, compounds A and B, show these product mixtures to also have characteristic gemini surfactant properties. Even though the dimer IIa representing the "average" molecular structure based on the stoichiometry is only one of many components in the mixture of oligomers, the composite produces a very desirable low critical micelle concentration and high $pC_{20}$ values. Both examples generated little foam, which would further suit them for oil field and industrial applications.

TABLE 1

Properties of Poly(Alkylamine Bis-ethoxylate Phosphates)

| Compound | CMC (M) | γ cmc (dyn/cm) | $pC_{20}$ | Foam Height (mm, 0 → 5 min) |
|---|---|---|---|---|
| Ex. 1[a] | $8.1 \times 10^{-6}$ | 34.5 | 7.2 | 58 → 30 |
| Ex. 2[a] | $3.8 \times 10^{-6}$ | 39.0 | 7.2 | 10 → 2 |
| A[1] | $6.3 \times 10^{-7}$ | 34.0 | 7.3 | 117 → 106 |
| B[1] | $3.5 \times 10^{-6}$ | 29.5 | 6.7 | — |
| Controls | | | | |
| Miranol Ultra[b] | $2.0 \times 10^{-4}$ | 26.5 | 5.4 | — |
| Miranol CS[a] | $5.6 \times 10^{-5}$ | 27.0 | 5.8 | — |

[a]0.1 M NaCl, pH 7.0
[b]0.1 M NaCl, pH 6.0

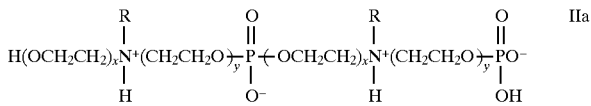

Ex. 1, R = Cocoalkyl ($C_{12,14}$), x + y = 5, x,y ≠ 0
Ex. 2, R = Tallowalkyl ($C_{16,18}$), x + y = 7, x,y ≠ 0

TABLE 1-continued

Properties of Poly(Alkylamine Bis-ethoxylate Phosphates)

| Compound | CMC (M) | γ cmc (dyn/cm) | $pC_{20}$ | Foam Height (mm, 0 → 5 min) |
|---|---|---|---|---|

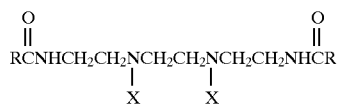

Compound A, R = $-C_{11}H_{23}$, X = $-CH_2CO_2^-Na^+$
Compound B, R = $-C_{11}H_{23}$, X = $-CH_2CH(OH)CH_2SO_3^-Na^+$
Miranol Ultra is a sodium cocoamidoamphoglycinate; a non-gemini amphoteric analog of Compound A.
Miranol CS is a sodium cocoamidoamphopropylsulfonate; a non-gemini amphoteric analog of Compound B.

What we claim is:

1. A surfactant composition comprising the formula:

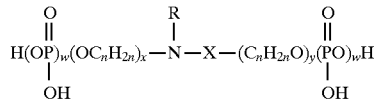

wherein X is:

$$\left[ (C_nH_{2n}O)_y \underset{OH}{\overset{\overset{O}{\|}}{P}} - \left[ O - \underset{OH}{\overset{\overset{O}{\|}}{P}} \right]_v -(OC_nH_{2n})_x - \underset{R_1}{N} \right]_m$$

wherein R and $R_1$ independently represent the same or different $C_1$ to $C_{36}$ straight or branched chain alkyl, alkylene, aryl, alkylaryl and arylalkyl, said R and $R_1$ optionally further characterized as containing ether, thioether, polyalkylene oxide, amine or quaternary ammonium, amide or ester groups; or are substituted thereby with the open valence filled by $R_3$ wherein $R_3$ is hydrogen or R, n is a whole number from 2 to about 4, m is a number of from 1 to 10, v is 0 or 1; w is 0, 1, or 2 with the further stipulation that both w's cannot be 0, and x and y are whole number integers of from 1–50.

2. The surfactant composition of claim 1 wherein R and $R_1$ can individually represent:

$$-CH_2CH_2\overset{\overset{O}{\|}}{N}R_2$$
$$\quad\quad\quad |$$
$$\quad\quad\quad (CH_2CH_2O)_zH$$

wherein $R_2$ independently is selected from the group defined by R and z is 0 or a whole integer.

3. The composition of claim 1 where v=0.

4. The composition of claim 1 represented by the formula:

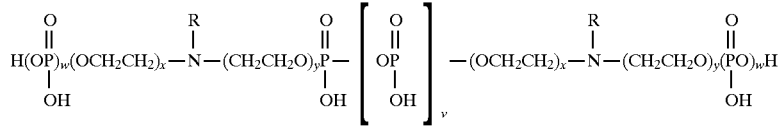

wherein R, v, w, x and y have been hereinbefore defined.

5. The composition of claim 1 represented by the formula:

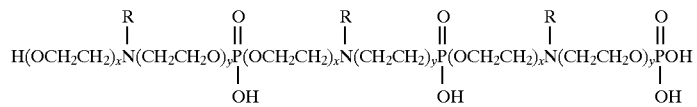

wherein R, x and y have been hereinbefore defined.

6. The composition of claim 1 represented by the formula:

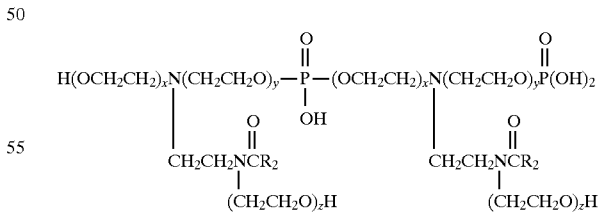

wherein $R_2$, x, and y have been hereinbefore defined and z is 0 or a whole integer.

7. The composition of claim 1 represented by the formula:

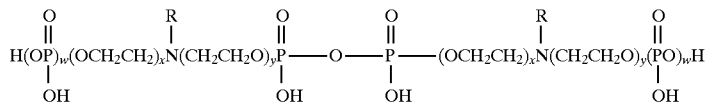

wherein R, w, x and y have been hereinbefore defined.

8. A blend of surfactants comprising a surfactant of the formula:

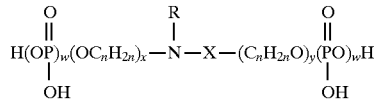

wherein X is:

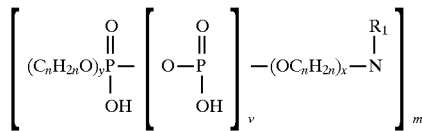

wherein R and $R_1$ independently represent the same or different $C_1$ to $C_{36}$ straight or branched chain alkyl, alkylene, aryl, alkylaryl and arylalkyl, said R and $R_1$ optionally further characterized as containing ether, thioether, polyalkylene oxide, amine or quaternary ammonium, amide or ester groups; or are substituted thereby with the open valence filled by $R_3$ wherein $R_3$ is hydrogen or R, n is a whole number from 2 to about 4, m is a number of from 1 to 10, v is 0 or 1; w is 0, 1, or 2 with the further stipulation that both w's cannot be 0, and x and y are whole number integers of from 1–50 and at least one additional surfactant selected from the group consisting of anionic surfactants, nonionic surfactants, cationic surfactants, amphoteric surfactants, zwitterionic surfactants and mixtures thereof.

9. The blend of surfactants of claim 8, wherein said nonionic surfactant is selected from the group consisting of fatty acid glycerine esters, sorbitan fatty acid esters, sucrose fatty acid esters, polyglycerine fatty acid esters, higher alcohol ethylene oxide adducts, single long chain polyoxyethylene alkyl ethers, polyoxyethylene alkyl allyl ethers, polyoxethylene lanolin alcohols, polyoxyethylene fatty acid esters, polyoxyethylene glycerine fatty acid esters, polyoxyethylene propylene glycol fatty acid esters, polyoxyethylene sorbitol fatty acid esters, polyoxyethylene castor oils or hardened castor oil derivatives, polyoxyethylene lanolin derivatives, polyoxethylene fatty acid amides, polyoxyethylene alkyl amines, alkyl pyrrolidones, glucamides, alkylpolyglucosides, mono- or dialkanol amides, mono- or diamides, polyoxyethylene alcohols, alkylamine oxides and mixtures thereof.

10. The blend of surfactants of claim 8, wherein said anionic surfactant is selected from the group consisting of fatty acid soaps, ether carboxylic acids and the salts thereof, alkane sulfonate salts, α-olefin sulfonate salts, the sulfonate salts of a higher fatty acid ester, higher alcohol sulfate ester salts, fatty alcohol ether sulfate salts, higher alcohol phosphate ester salts, fatty alcohol ether phosphate ester salts, condensates of higher fatty acids and amino acids, collagen hydrolysate derivatives and mixtures thereof.

11. The blend of surfactants of claim 8, wherein said cationic surfactant is selected from the group consisting of alkyltrimethylammonium salts, dialkyldimethylammonium salts, alkyldimethylbenzylammonium salts, benzethonium chlorides, acylamino acid-type cationic surfactants and mixtures thereof.

12. The blend of surfactants of claim 8, wherein said amphoteric surfactant is selected from the group consisting of an amino acids, betaines, sultaines, phosphobetaines, imidazoline-type amphoteric surfactants, soybean phospholipids, yolk lecithins and mixtures thereof.

13. The blend of surfactants of claim 8 further comprising an auxiliary additive.

14. The blend of surfactants of claim 13, wherein said auxiliary additive is selected from the group consisting of an inorganic salt such as Glauber salt and common salt, a builder, a humectant, a solubilizing agent, a UV absorber, a softener, a chelating agent, a viscosity modifier and mixtures thereof.

15. A cleaning composition comprising an aqueous solution having a cleaningly effective amount of the composition of claim 8 dissolved therein.

16. The cleaning composition of claim 15, wherein the solution is selected from the group consisting of hair shampoos, baby shampoos, body shampoos, bubble baths, liquid and bar soaps, bath gels, hair conditioning gels, skin creams and lotions, skin contacting cosmetics, make-up removal creams and lotions, liquid detergents, dish detergents, liquid soaps, bleach activators, bleach stabilizers and the like.

17. The cleaning composition of claim 15, wherein the solution is selected from the group consisting of hard surface cleaners, emulsion polymerization additives, laundry and dish detergents, carpet cleaners, lubricants, anti-wear, anti-corrosion and anti-scaling additives, metal cleaning, cutting or grinding aids, gellants and viscosity control agents (shear sensitive thickeners) and textile processing aids.

* * * * *